US010751219B2

(12) United States Patent
Vaughan et al.

(10) Patent No.: US 10,751,219 B2
(45) Date of Patent: *Aug. 25, 2020

(54) TYMPANSOSTOMY TUBE AND INSERTION DEVICE

(71) Applicant: CORK INSTITUTE OF TECHNOLOGY, Cork (IE)

(72) Inventors: John Vaughan, Cork (IE); Olive O'Driscoll, Kinsale (IE)

(73) Assignee: CORK INSTITUTE OF TECHNOLOGY, Cork (IE)

( * ) Notice: Subject to any disclaimer, the term of this patent is extended or adjusted under 35 U.S.C. 154(b) by 244 days.

This patent is subject to a terminal disclaimer.

(21) Appl. No.: 15/981,655

(22) Filed: May 16, 2018

(65) Prior Publication Data

US 2018/0256400 A1     Sep. 13, 2018

Related U.S. Application Data

(63) Continuation of application No. 14/441,145, filed as application No. PCT/EP2013/073016 on Nov. 5, 2013, now Pat. No. 10,016,303.

(60) Provisional application No. 61/726,660, filed on Nov. 15, 2012.

(51) Int. Cl.
*A61F 11/00* (2006.01)
*A61B 17/00* (2006.01)

(52) U.S. Cl.
CPC ... *A61F 11/002* (2013.01); *A61B 2017/00424* (2013.01); *A61F 2250/001* (2013.01); *A61F 2250/0001* (2013.01); *A61F 2250/0039* (2013.01)

(58) Field of Classification Search
CPC ...... A61F 11/002; A61F 11/00; A61F 11/004; A61F 11/008; A61B 2017/0046; A61B 2017/00623
See application file for complete search history.

(56) References Cited

U.S. PATENT DOCUMENTS

| 3,948,271 | A | * | 4/1976 | Akiyama | ............. | A61F 11/002 604/540 |
| 4,766,886 | A | * | 8/1988 | Juhn | ..................... | A61B 1/227 600/200 |
| 5,053,040 | A | | 10/1991 | Goldsmith, III | | |

(Continued)

FOREIGN PATENT DOCUMENTS

WO     2003/057082 A1    7/2003

OTHER PUBLICATIONS

International Search Report; PCT/EP2013/073016; dated Mar. 4, 2014.

*Primary Examiner* — Alexander J Orkin
(74) *Attorney, Agent, or Firm* — Studebaker & Brackett PC

(57) ABSTRACT

A tympanostomy tube applicator has a hand-held housing and a stem extending from the housing and having a shape arranged for engagement in the ear canal. A tympanostomy tube inserter has a user actuator, a rod having a tip to pierce a patient's tympanic membrane and to support a tympanostomy tube through the membrane where it is pierced. The inserter inserts a collapsed tympanostomy tube through the membrane and expands the tube in situ to provide a distal flange in the tympanostomy tube. A myrongotomy tip expands the tube to a final state having a distal flange as it is retracted.

19 Claims, 12 Drawing Sheets

(56) References Cited

U.S. PATENT DOCUMENTS

| | | | |
|---|---|---|---|
| 5,496,329 | A | 3/1996 | Reisinger |
| 10,016,303 | B2 * | 7/2018 | Vaughan ............... A61F 11/002 |
| 2003/0070676 | A1 | 4/2003 | Cooper et al. |
| 2003/0120292 | A1 | 6/2003 | Park et al. |
| 2005/0060044 | A1 | 3/2005 | Roschak et al. |
| 2009/0099573 | A1 | 4/2009 | Gonzales |
| 2009/0209972 | A1 | 8/2009 | Loushin et al. |
| 2012/0150119 | A1 | 6/2012 | Schaeffer et al. |
| 2013/0030545 | A1 | 1/2013 | Gross et al. |
| 2013/0338678 | A1 | 12/2013 | Loushin et al. |
| 2014/0094733 | A1 | 4/2014 | Clopp et al. |

* cited by examiner

TYMPANSOSTOMY TUBE AND INSERTION DEVICE

FIELD OF THE INVENTION

The invention relates to insertion of a tympanostomy tube ("grommet") into the tympanic membrane.

PRIOR ART DISCUSSION

A tympanostomy tube (also known as a tube) is a small tube inserted into the tympanic membrane in order to ventilate the middle ear for a prolonged period of time, and to prevent the accumulation of fluid in the middle ear. The tube is usually inserted under general aesthetic in a surgical environment. The surgeon will use various tools to firstly clean the outer ear canal, will then use a myringotomy knife to make an incision in the tympanic membrane, and will then use a suction tip to remove fluid from the middle ear. Finally, the surgeon will use a combination of forceps and probe to insert the tympanostomy tube.

US2009/0209972 (Loushin) describes an insertion device which deforms the ends of a ventilation device to a flange-like structure. It does so by use of a bumper or stop on a cutting member. The bumper or stop may be inflatable.

US2009/0099573 (Gonzales) describes a device for inserting a tympanostomy tube.

The invention is directed towards achieving a simpler procedure.

SUMMARY OF THE INVENTION

According to the invention, there is provided a tympanostomy tube applicator comprising:
- a hand-held housing,
- a stem extending from the housing and having a shape arranged for engagement in the ear canal; and
- a tympanostomy tube inserter,
- wherein the housing includes at least one user actuator for operation of the inserter,
- wherein the inserter comprises a rod having a tip to pierce a patient's tympanic membrane and to support a collapsed tympanostomy tube through the membrane where it is pierced; and
- wherein the inserter is adapted to expand from within a distal end of the collapsed tympanostomy tube to provide in situ a distal flange in the tympanostomy tube.

By pressing the tube from within at the distal end at least, the applicator can reliably re-configure the tube in situ so that the desired shape is formed to enable the tube remain in place for the desired time duration post-surgery. Such a tube expansion action is more repeatable and effective than the prior art axial pressing approach.

In one embodiment, the inserter comprises a non-inflatable feature adapted to be pulled through the collapsed tube to expand the tube. In one embodiment, said feature has a curved surface for engagement with the tube to expand it as the feature is pulled through.

In one embodiment, said surface is on a proximal side of the feature and is curved and narrows towards the proximal direction.

In one embodiment, the inserter comprises a shoulder to act as a proximal stop for the tympanostomy tube during expansion of the tympanostomy tube.

In one embodiment, the collapsed tube comprises distal guide members having outer surfaces with a radial inward component to assist guiding of the tube through a patient's tympanic membrane. Preferably, the guide members are configured to form part of the distal flange after insertion. In one embodiment, the collapsed tube comprises slots or slits between said guide members as reliefs to assist expansion.

In another embodiment, the applicator comprises a handle with the actuator and a cartridge with the stem, the cartridge being releasably connected to the handle. In one embodiment, the cartridge includes a distal part of the inserter which is adapted to connect with a proximal part of the inserter within the handle when the cartridge is connected to the handle.

Preferably, the inserter comprises a non-inflatable feature adapted to be pulled through the collapsed tube to expand the tube, the inserter comprises a spring mechanism to pull the feature through the tube, the cartridge is adapted to load the spring mechanism as it is connected to the handle, and the actuator is adapted to release the spring mechanism to pull the feature.

In one embodiment, the cartridge is adapted to be connected to the handle in a rotational and translational action, said action causing the spring mechanism to load.

In one embodiment, a plug in the handle or the cartridge engages in a socket in the other of the handle or the cartridge, and inter-engaging features cause a spring of the spring mechanism to be loaded as the cartridge is connected to the handle.

In a further embodiment, the actuator comprises a single button protruding from the housing. In one embodiment, the cartridge is pre-loaded with the tube and the tube is non-removable except by operation of the inserter.

In one embodiment, the inserter comprises a balloon and means to inflate the balloon to expand the collapsed tube. Preferably, the balloon is located proximally of the piercing tip.

In one embodiment, the stem is in the form of a speculum and includes a channel for an endoscope arranged alongside the inserter. In one embodiment, the housing has an endoscope guide along a side of the housing. In one embodiment, the applicator further comprises a jig for calibration of focal point of the endoscope to a known distance before insertion. In one embodiment, the jig comprises a flange for engagement with the head and a flange for providing a visible plane at a known focusing distance.

In one embodiment, the applicator further comprises a guide collar for the head, said guide collar being configured to engage the patient's ear proximally of the ear canal. In one embodiment, the applicator further comprises an adjustment mechanism for adjusting longitudinal position of the guide collar with respect to the head.

In another aspect, the invention provides a tympanostomy tube comprising a proximal flange and a shank configured to expand with application of force from within to form in situ a distal flange and a central duct portion.

In one embodiment, the shank forms an initial distal flange and said initial distal flange has slits of slots to facilitate expansion.

In one embodiment, the original distal flange is configured to expand in the radial dimension to an extent of 20% to 60%.

In one embodiment, the shank is tapered at a distal end with a curved external surface narrowing in the distal direction. Preferably, the tapered distal end comprises circumferentially spaced-apart guide members. In one embodiment, the tube comprises a preliminary distal flange and said guide members extend from said preliminary distal flange.

In one embodiment, the tube is of a material having a plastic region in a stress vs. strain curve so that force applied causes it to become plastic and permanently deform with expansion of the distal end of the shank to an extent in the range of 20% to 60%.

DETAILED DESCRIPTION OF THE INVENTION

Brief Description of the Drawings

The invention will be more clearly understood from the following description of some embodiments thereof, given by way of example only with reference to the accompanying drawings in which:—

DESCRIPTION OF THE EMBODIMENT

Figure 1:
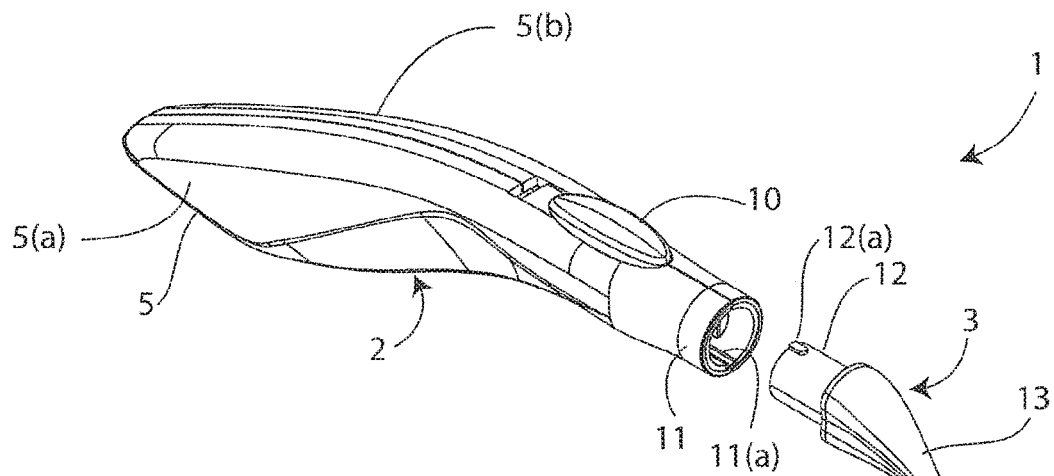
FIG. 1 is a perspective view from above of an insertion device or applicator of the invention with handle and stem parts separated.
Figure 2:
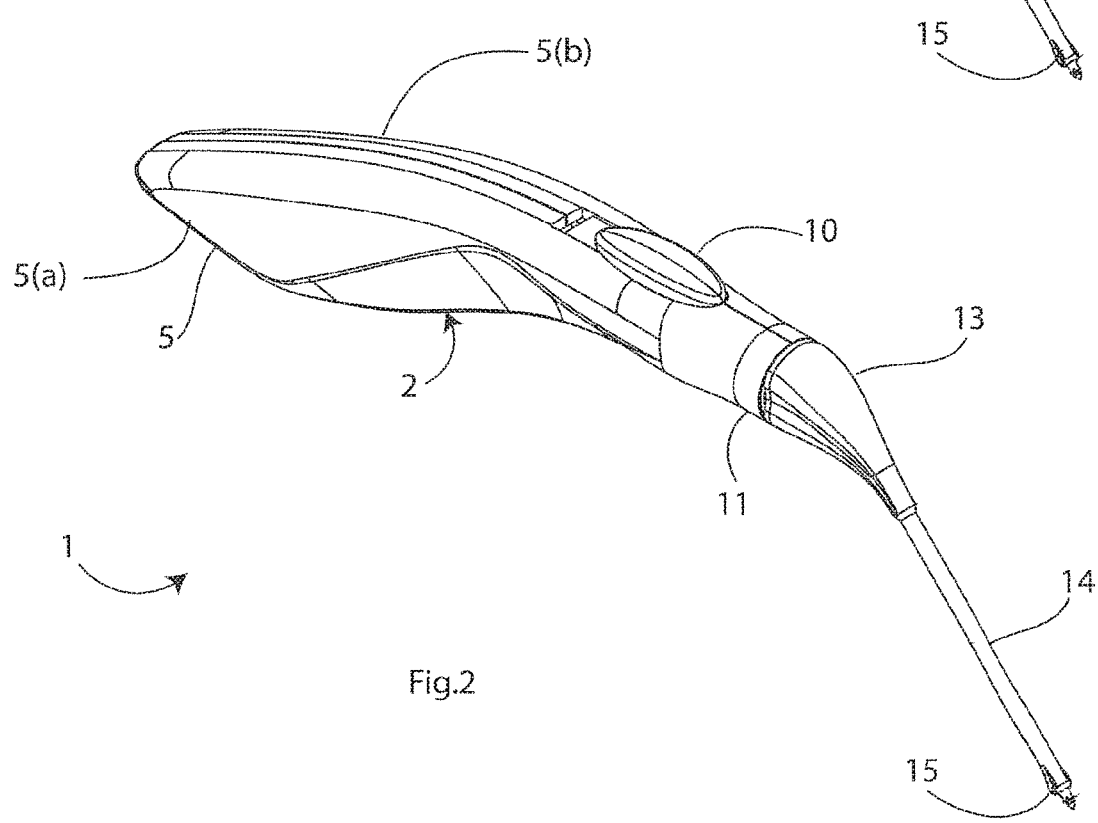
FIGS. 2 and 3 are perspective views when these parts are connected.

Referring to FIGS. 1 to 9 a tympanostomy tube (sometimes referred to as a "grommet") applicator or insertion device 1 comprises a handle 2 and a cartridge 3. The handle 2 has a housing 5 shaped for ergonomic gripping, and a press-button 10 for operation. Also there is a socket 11 to receive a plug 12 of the cartridge 3. The cartridge 3 has a housing 13 which is beat to one side at its distal end, where it supports a stem 14 terminating in a tip 15. The stem 14 of the cartridge 3 is flexible enough to deform to the desired shape during insertion, yet is resistant to compression. It includes a steel helical spring (FIG. 6, 14(a)) within the stem 14 to allow flexure but good compression strength.

The cartridge is pre-assembled with a tympanostomy tube 60, and so is for single use on one ear. Its connection to the handle 2 is a twisting mad pushing action which has the dual purpose of connecting the cartridge 3 to the handle 2 and also compressing a spring, release of which will subsequently provide the force or tube 60 deformation in situ. The tube has a diameter of 2.5 mm as is typical for a tube of the type known as the "Shepard" type of tympanostomy tube. When the tube 60 has been inserted in one ear, the empty cartridge is removed and a second (loaded) cartridge is connected to the handle for the second ear if required (as is often the case). When this tube has been inserted into the second ear the handle 2 is disposed of. However, the handle 2 may be used if desired with additional loaded cartridges, for example for a further patient or upon premature activation of the trigger 10.

Figure 3:
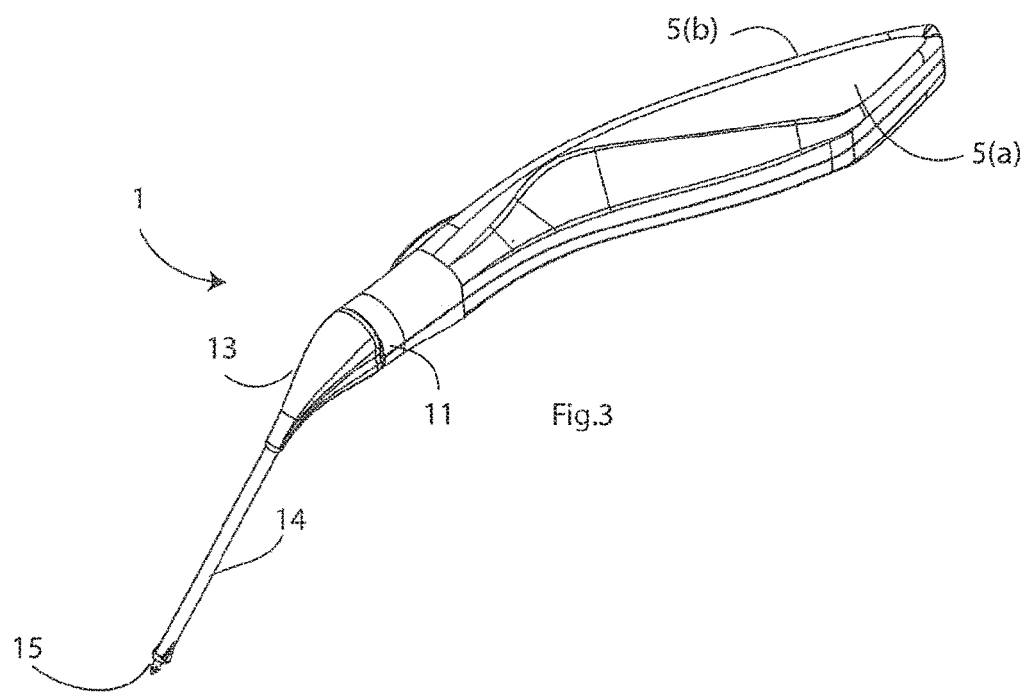

The handle 2 is made up of two ergonomic case moulded plastics halves 5(a) and 5(b). The cartridge 3 is also made from components 13(a) and 13(b) which snap fit together during assembly. The cartridge plug 12 has a tab 12(a) which mates with a slot 11(a) in the socket 11. Once the cartridge plug 12 is fully inserted into the handle socket 11 the cartridge 3 is rotated to lock it into place. On further rotation of the cartridge 3, the tab 12(a) locks into different mating parts of the slot 11(a), which provides the user with different variations of device setup. FIG. 3 shows the cartridge 3 set at 90° to the handle 2.

Figure 4:
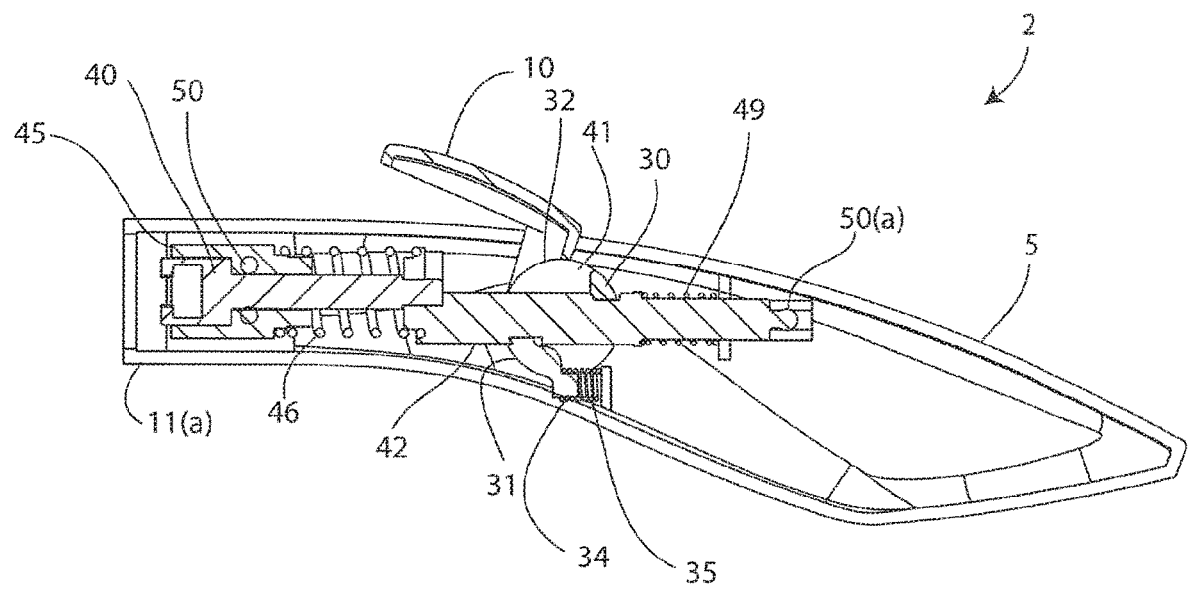
FIGS. 4 to 7 are cross-sectional views of the handle part, the stem part, the stem tip, and the full device respectively.

FIG. 4 shows a sectioned view of the handle 2 in a resting configuration prior to connection of the cartridge 3. The handle button 10 has ratchets 30 and 31 which are attached to a rotating drum 32. A part 34 of the drum 32 houses a return spring 35 to provide upward bias to the button 10. The ratchets 30 and 31 mate with a slider 40 which has opposing ratchet teeth 41 and 42. A compression component 45 is mated coaxially to the slider 40 and both are assembled within a compression spring 46. A rubber ring 50 is housed within the compression component 45 to provide damping during use, and there is a complementary damper sleeve 50(a) at the opposite (right side as viewed in FIG. 4) end of the slider 40. As shown by this drawing the slider 40 is in two parts for manufacturing purposes, however, it may alternatively be moulded as an integral component. There is a return spring 49 for the slider 40.

Figure 5:
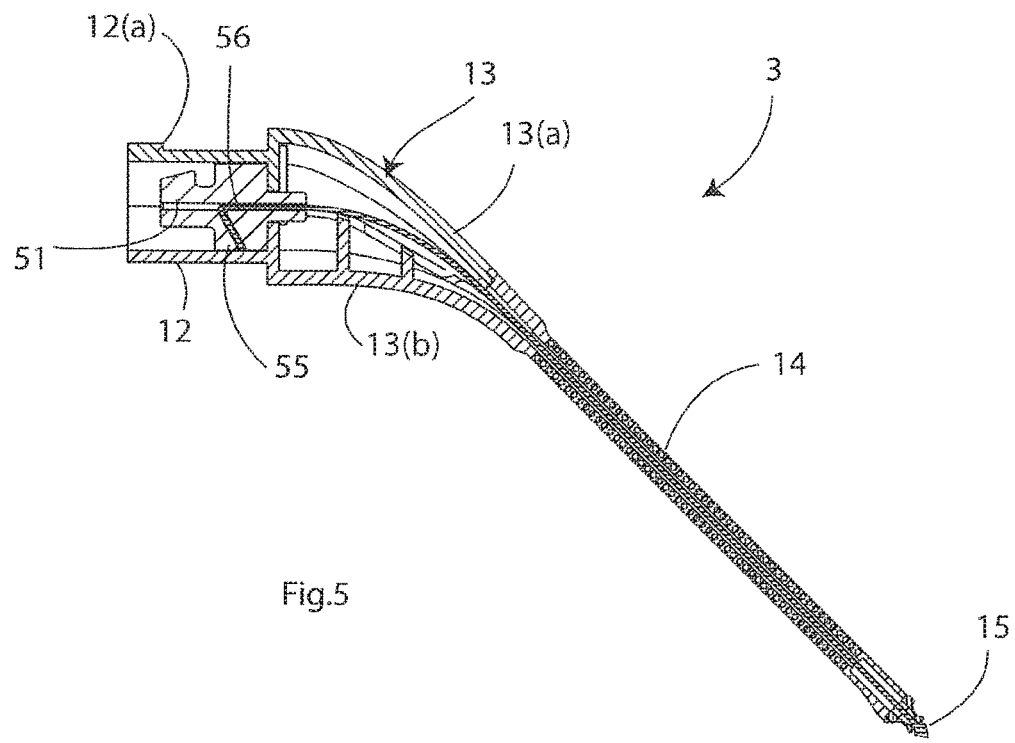
Figure 6:
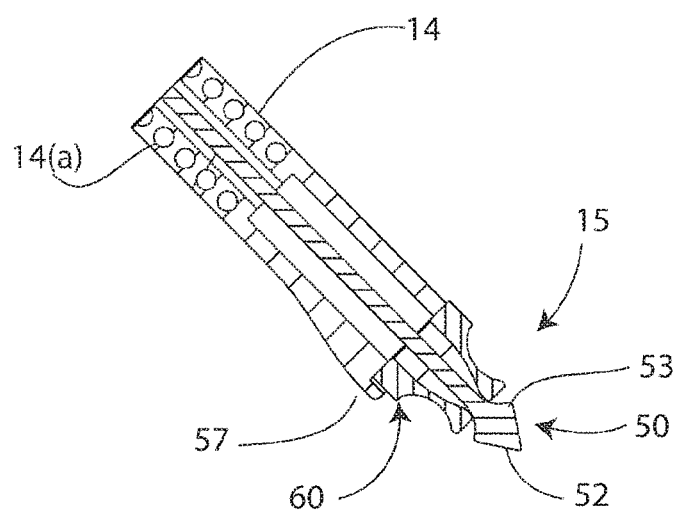

Referring to FIGS. 5 and 6, the cartridge 3 has a myringotomy knife 50 the distal end of which has a sharp tip 52 for cutting through the tympanic membrane. Behind the tip 52 there is a surface 53 which is curved and narrows towards the proximal side, for use in deforming the tube 60 as described in more detail below. Immediately proximal to the myringotomy knife tip 52 there is a tympanostomy tube 60 in a collapsed state. The myringotomy knife 50 has a contoured surface 53 which is configured to deform the tympanostomy tube 60 during deployment by expanding it from within. The myringotomy knife 50 is connected to a puller component 51 via a flexible shaft 56 which trains through the stem 14. A bent feature 55 at the proximal end ensures that it stays in contact with the pull component 51 throughout deployment. The pull component 51 connects with the slider component 40 within the handle 2 when the cartridge 3 is connected to the handle 2.

The distal end of the stem 14 has a lip 57 fitting laterally against and extending around almost the full circumference of the side of a tube 60. In addition to helping to secure the tube 60 this also widens the stem end so that it acts as a stop to prevent unintentional excessive insertion, and also assists with location of the knife tip 52.

As shown most clearly in FIGS. 8(a) to 8(f) the tube 60 has a proximal (or "outer") pre-formed flange 61, a central ventilation duct 62, and a distal (or "inner") flange 63 with slots 64. The flange 63 has a diameter which is smaller than that of the proximal flange 61 by about 30% to 40%. There are also lead-in guide members 65 in the form of fingers extending generally axially from the distal flange 63. There is one slot 64 between each guide member 65. The slots 64 are grooves which do not penetrate for the full depth of the wall of the tube 60. In general their depth is in the range of about 20% to 90% of the wall depth, and preferably about 80%.

As is clear from FIG. 8 the tube 60 as provided in the cartridge 3 already has a distal flange (63), however as noted above this has a diameter less than that of the proximal flange 61. However, the distal flange 63 does not present a problem for insertion through the TM because of the action of the guide members 65. The latter have external surfaces which are tapered with a radial component which is inward and so allow streamlined insertion through the cut which has been made by the knife tip 52.

In use, as described above the surgeon connects the cartridge 3 to the handle by engaging the plug 12 in the socket 11 and rotating and pushing the cartridge 3 so that it is fully engaged and at the same time compresses the spring 46 so that it is loaded. The surgeon then moves the stem 14 through the ear canal and punctures the tympanic membrane using the myringotomy knife tip 52. Continued movement pushes through until the inner flange 63 and the outer flange 61 are on opposite sides of the tympanic membrane. The lip 57 helps to prevent the surgeon from pushing the stem 14 too far into the middle ear; this feature acting as a backstop. To deform the tympanostomy tube 60, the surgeon merely presses the handle button 10. This causes the mechanical advantage within the handle 2 to pull on the slider component 51. This in turn pulls the distal tip 52 of the myringotomy knife 50 through the tympanostomy tube 60, causing the tympanostomy tube 60 to deform and release from the device 1. This movement is shown in FIGS. 8(*a*) to 8(*f*).

Figure 7:
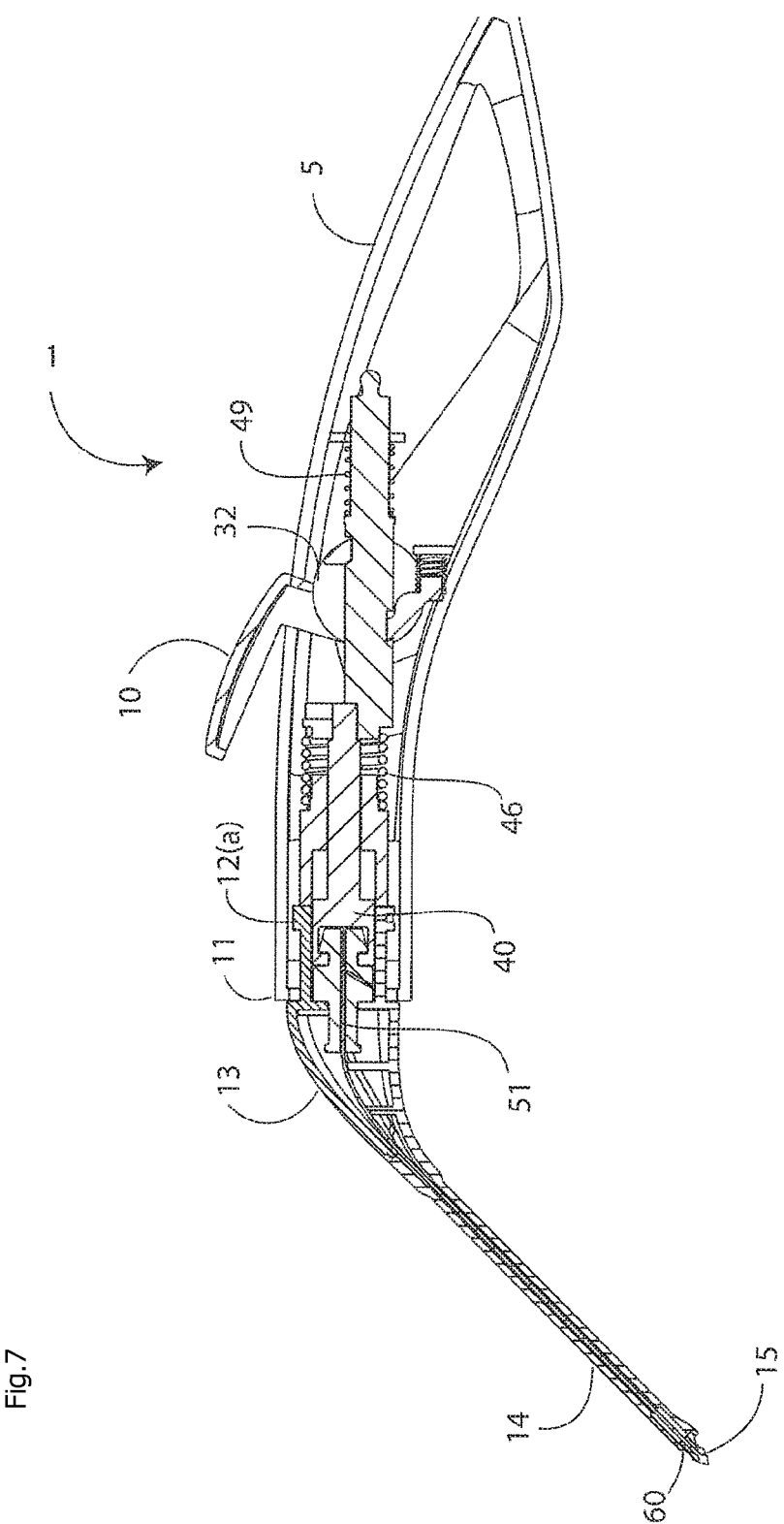
Figure 8A:
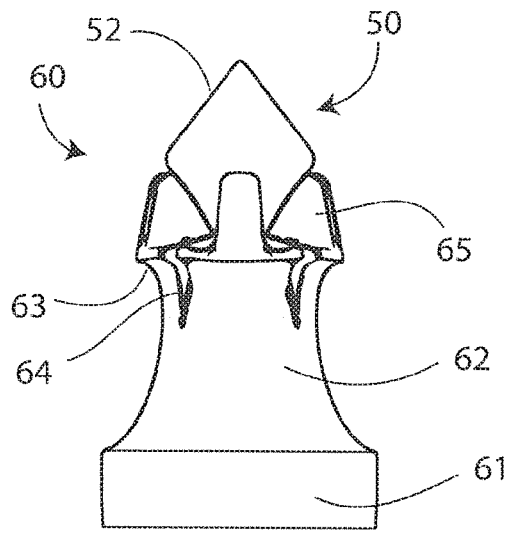
FIGS. 8(a) to 8(f) are a series of diagrams illustrating deformation of a tympanostomy tube during insertion.
Figure 8B:
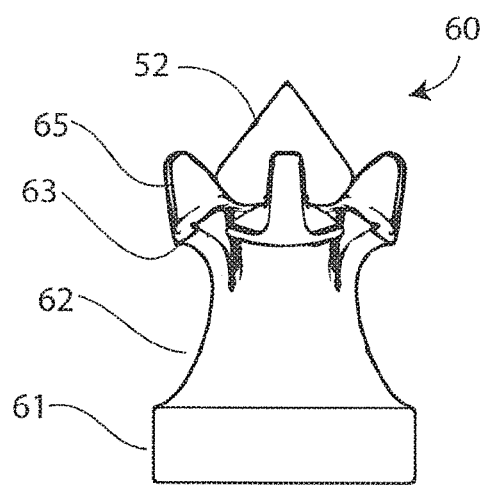
Figure 8C:
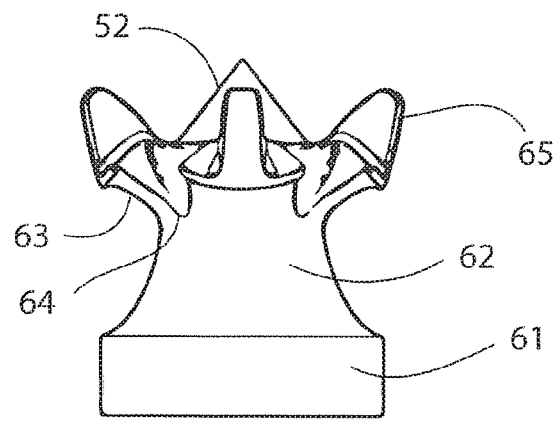
Figure 8D:
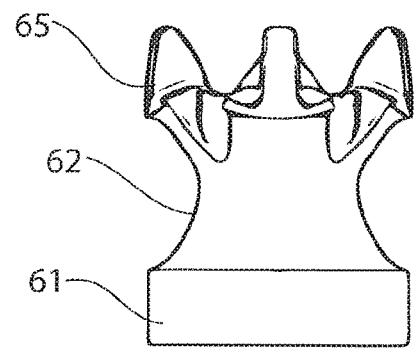
Figure 8E:
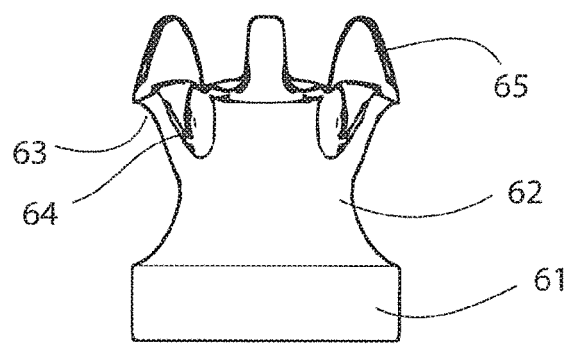
Figure 8F:
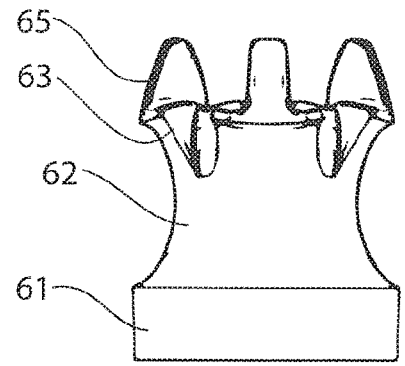

FIG. 7 shows the cartridge 3 assembled into the handle 2 and the device 1 in the primed configuration prior to tube 60 deployment. When the cartridge plug 12 is pushed into the handle socket 11 this pushes on the compression component 45 which in turn compresses the spring 46.

The user then locks the cartridge 3 into the handle 2 by rotating the cartridge 3, causing the tab 12(*a*) to lock into place. When the user pushes the button 10 this rotates the button drum 32 which also pushes against the spring 35. This disengages the drum ratchets 30 and 31 from the slider ratchet 41 and 42 and thereby releases the slider 40 to move under the force of the compression spring 46 which in turn actuates the cartridge slider component 51 which is connected to the myringotomy knife 50. The myringotomy knife tip 52 deforms the tympanostomy tube 60 and releases it from the cartridge 3. The speed at which the myringotomy knife tip 52 retracts through the tympanostomy tube 60 can be tuned by varying the stiffness of the compression spring 46.

To reset the system to the resting configuration the user rotates the cartridge 3 from its locked position within the handle 2 and removes the cartridge 3. This releases the compression component 45 and the return spring 49 resets all components to the initial position shown in FIG. 4.

In more detail, FIG. 8 shows five steps of the myringotomy knife tip 52 deforming the tympanostomy tube 60, after it has been located with the assistance of the guides 65. As the proximal surface 53 of the myringotomy knife tip 52 contacts the tympanostomy tube 60, the surface's angle and slight concave shape causes the tympanostomy tube 60 to both expand radially and compress axially. The tympanostomy tube 60 relief slots 64 on the inner flange 63 allow the tympanostomy tube 60 to deform to the correct shape. The inner flange 63 only increases in diameter by about 20% to 60%, and preferably in the range of 25% to 40%, however this is sufficient for adequate placement of the tube 60. It will be appreciated that the action of pulling through the tip only needs to achieve a limited, gradual and therefore predictable deformation of the tube 60. The tube's distal (inner) end only needs to turn through about 40° to reach the point of having the same diameter as the proximal flange.

Figure 9:
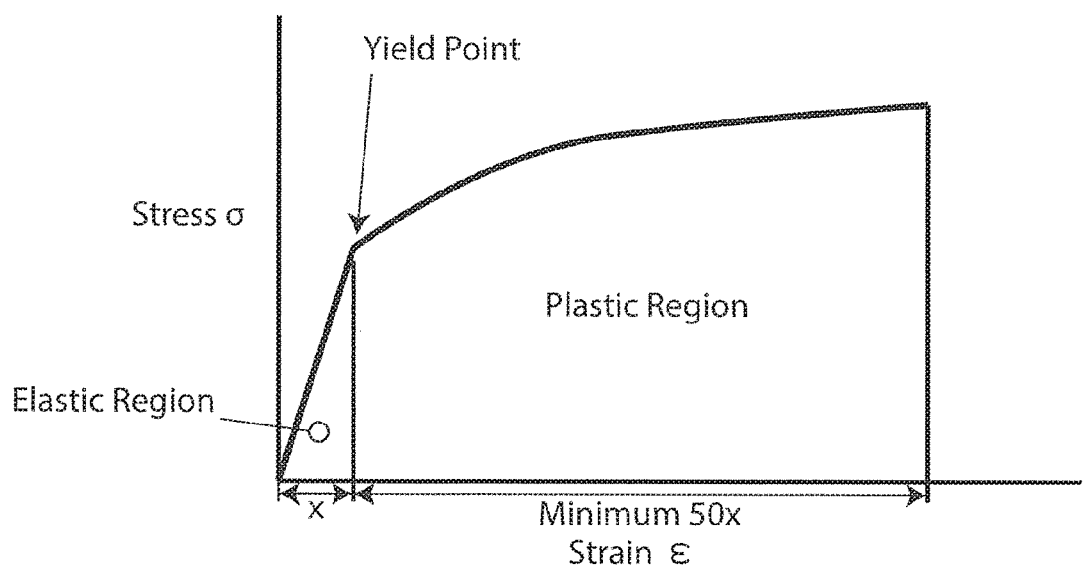
FIG. 9 is a plot showing tube material deformation characteristics.
Figure 10:
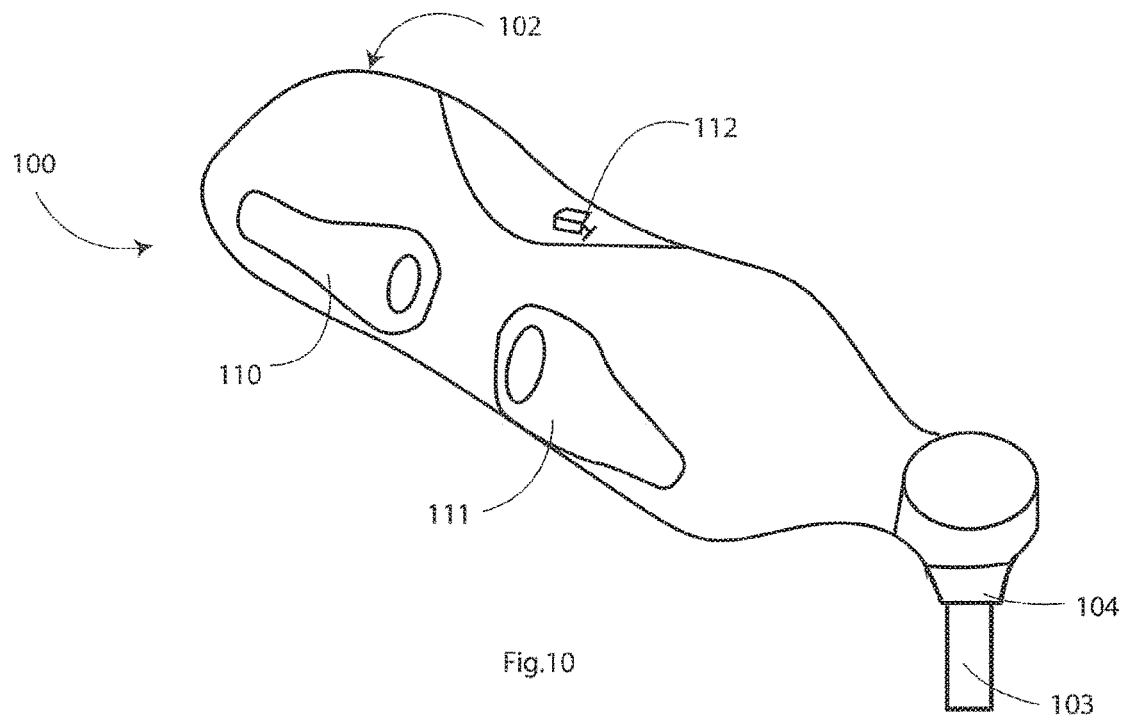
FIGS. 10 and 11 are perspective views of a tympanostomy tube applicator of the invention in another embodiment.
Figure 11:
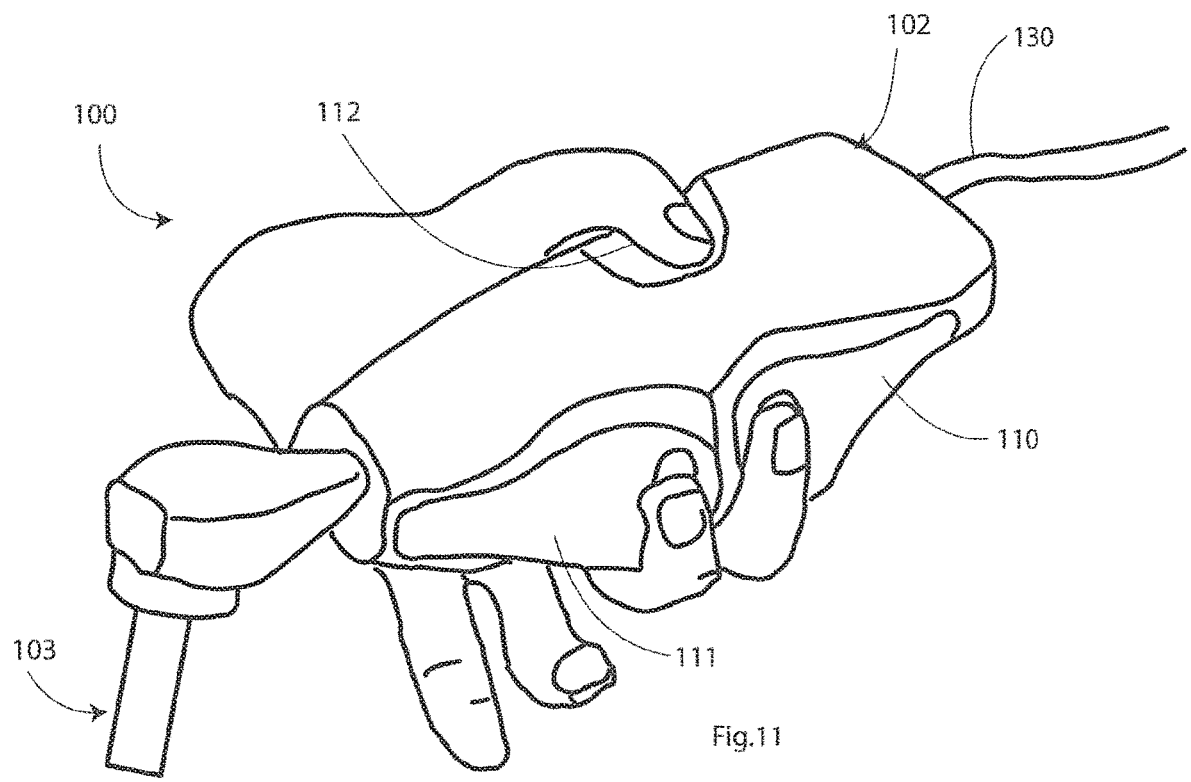

The mechanical stress strain characteristics of the material used in the tympanostomy tube 60 is advantageous to its correct function and deployment. The ideal material has a low elongation at the material yield point relative to its total elongation during plastic deformation. The plastic region of the stress strain curve would be at a minimum 50 times the elastic region of the stress strain curve with respect to material elongation. This relationship is shown in FIG. 9.

The tube 60 is suitable for the surgical application of temporarily ventilating the ear for a period of about 9 months, and the general type is typically referred to as the "Shepard" type. However, the tympanostomy tube may in other embodiments be of a different shape such as those known widely as the "Paperella" tube, or alternatively as the "Reuter Bobbin" tube. Where the shape is for a permanent insertion the type known as the "T-Tube" may be used. These know shapes are the final outline shapes after deformation.

It will be appreciated from FIG. 8 that, in addition to the distal flange 63 expanding to its permanent shape, the guide members 65 change gradually from an orientation with an inward radial component (FIG. 8(*a*)) to having an outward radial component (FIGS. 8(*b*) and 8(*c*)), and then back again to the inward direction (FIGS. 8(*d*) to 8(*f*)). The guide members 65 hence play a role during tube 60 expansion, namely helping to retain the correct tube position by exaggerating the inner flange temporarily as the tip 52 is retracted. It is envisaged that in other embodiments, the guide members 65 will be configured to be splayed out after tube deformation, thereby permanently enlarging the distal flange.

It will also be appreciated that the device 1 makes the surgical task of tube insertion simpler, with less room for error. The spring for retraction is automatically loaded by the single action of twisting the cartridge onto the handle, and so this can not be inadvertently omitted. Also, the device 1 more importantly allows the surgeon to locate accurately the tube and deform it in situ with little risk of movement during deformation because the only action required is pressing the button 10 to release the pre-loaded spring for retraction.

Figure 12:
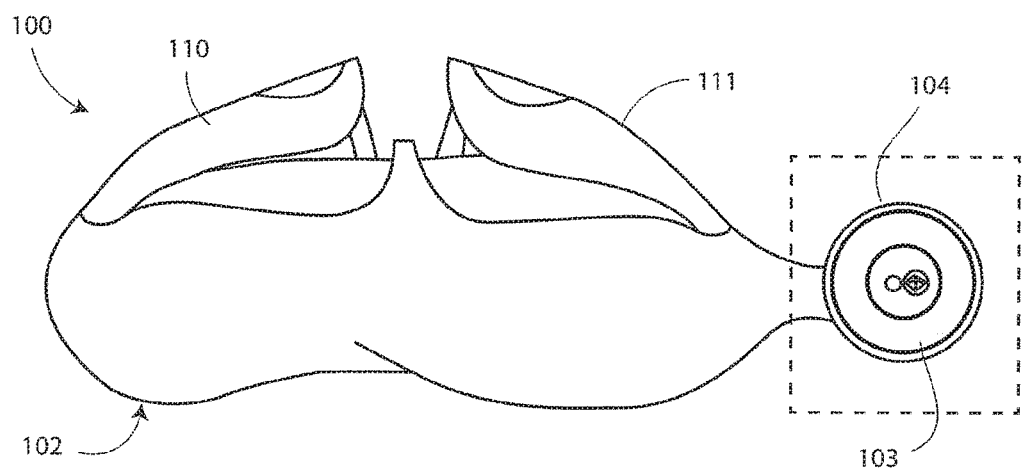
FIG. 12 is a side view of the applicator.
Figure 13:
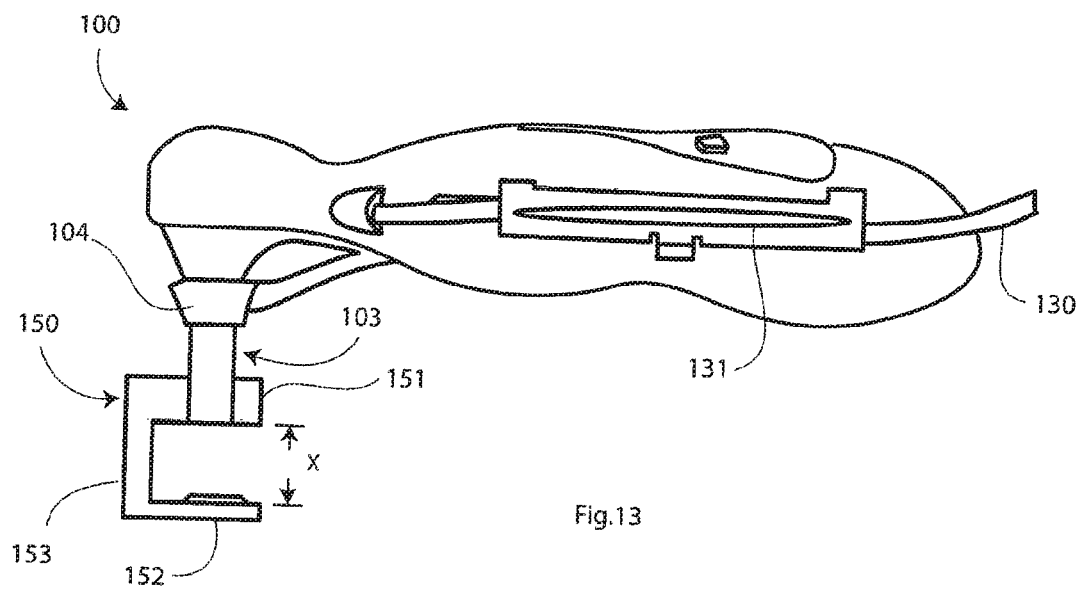
FIG. 13 is a side view showing calibration of the device.
Figure 14:
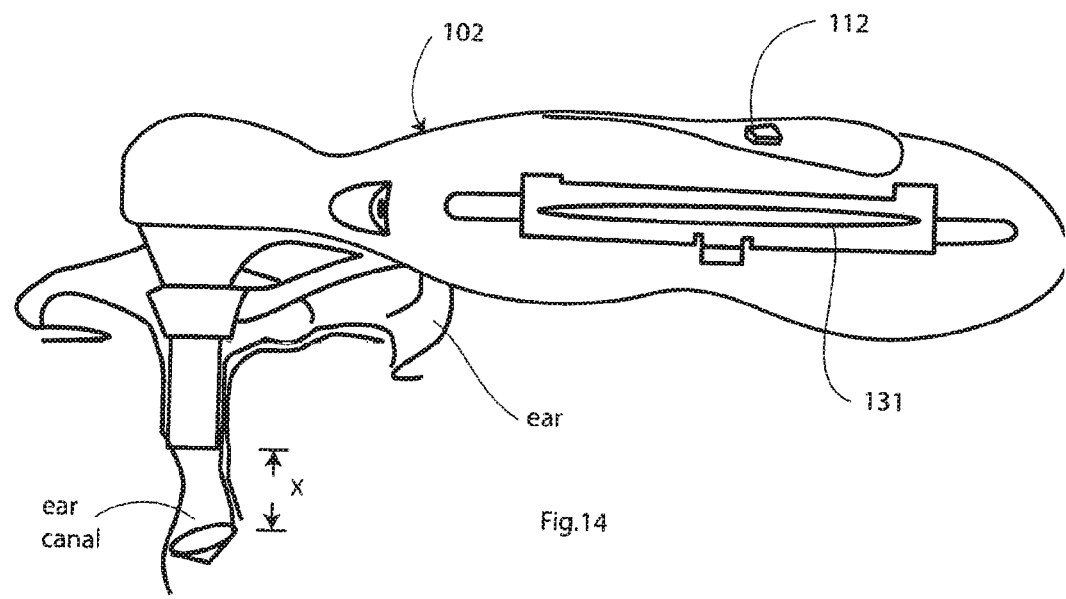
FIG. 14 shows it in use.
Figure 15:
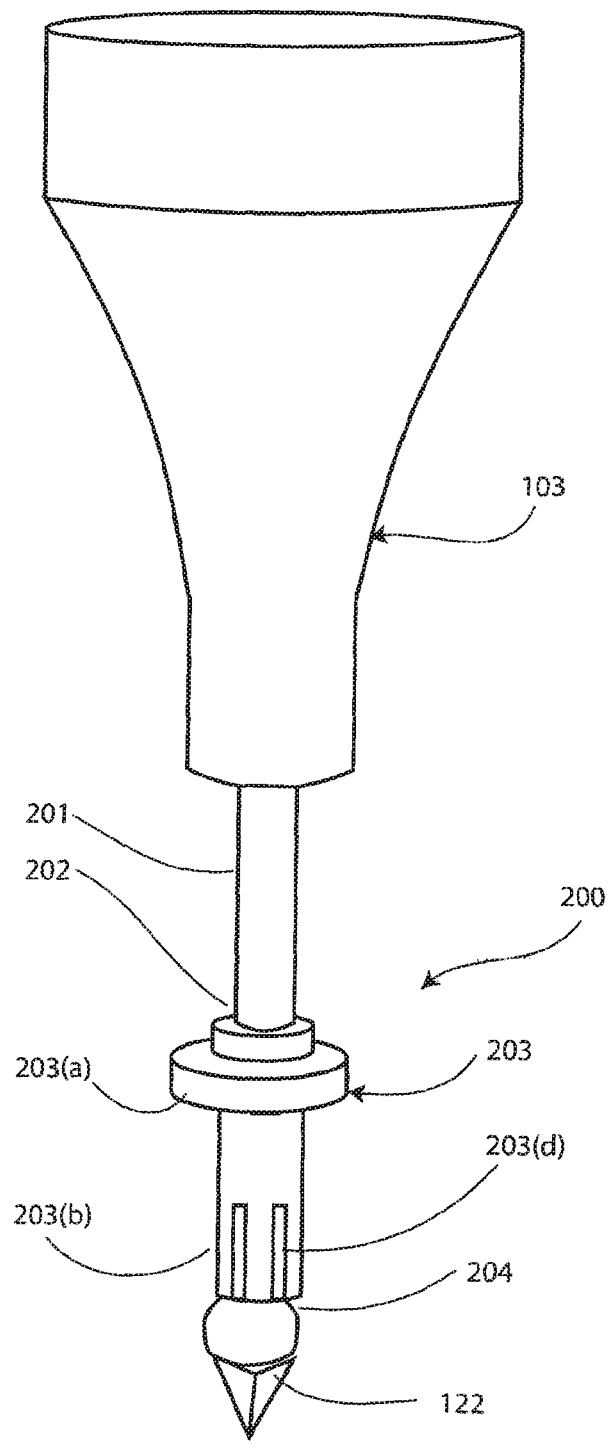
FIGS. 15, 16, 17 and 18 are enlarged side views of the head of the applicator in use deploying a tube.

Referring to FIGS. 10 to 17 a tube applicator 100 comprises a housing 102 arranged for single-handed grip, and a stem or head 103 with a guide collar 104. The head is arranged for head rotation about an axis through the housing 102. A guide collar 104 surrounds the head 103. There are triggers 110 and 111 and a guide collar adjustment button 112. An endoscope 130 can be trained through a holder 131 and terminate in a lens 120 in the head 103, as shown in FIGS. 12 to 14.

The head 103 further comprises an insertion assembly 200 having a sleeve-shaped stem 201, a shoulder 202. A rod (not shown) extends through the stem 201 and terminates in an inverted pyramid-shaped tip 122. The tip 122 has an upper face on which there is a balloon 204 and a tube 203 in a collapsed configuration.

The head 103 at the distal end of the device is indexable with rotation about an axis extending through the housing 102, with an allowed 180° rotation so that it may be used by either left or right-banded uses. It has a cylindrical body portion, which can enter the patient's ear canal. The guide collar 4 can adjust the distance between the tip of the cylindrical body and the tympanic membrane.

There is a channel within the device to accept a standard endoscope 130. This is formed by the endoscope guide 131 and the head 103. The endoscope 130 is pushed through the channel by the user until its lens 120 arrives at the tip of the head 103. FIG. 12 shows a detailed view of the head cylindrical body, it shows the distal end 120 of the endoscope 130 and the pyramid-shaped myringotomy blade tip 122 which is housed within the bead 103.

Prior to operation of the device, the endoscope is calibrated and focused using a focus calibration jig 150, shown in FIG. 13. The jig 150 comprises a top flange 151 connected to a bottom flange 151 by a web 153. Calibration is done by placing the tip of the head 103 in a hole in the top flange 151 of the jig 150. The endoscope is manipulated and focused until a target provided by the top surface of the lower flange 152 is in sharp focus on the video screen of the endoscope 130. This step is to ensure that the focal length of the endoscope 130 is at a fixed distance 'X' from the tip of the cylindrical body.

In use, the trigger 111 is operated to cause the insertion assembly 200 to extend from the head 103. The collapsed tube 203 comprises a proximal flange 203(a), and a shank 203(b) with slits 203(d).

The clinician's index and middle fingers are placed on both of the triggers 110 and 111. Her thumb is placed on the button 112, and the ring and small fingers are free to rest on the patient's face to detect any movement during the procedure. The patient is typically a child.

Figure 16:
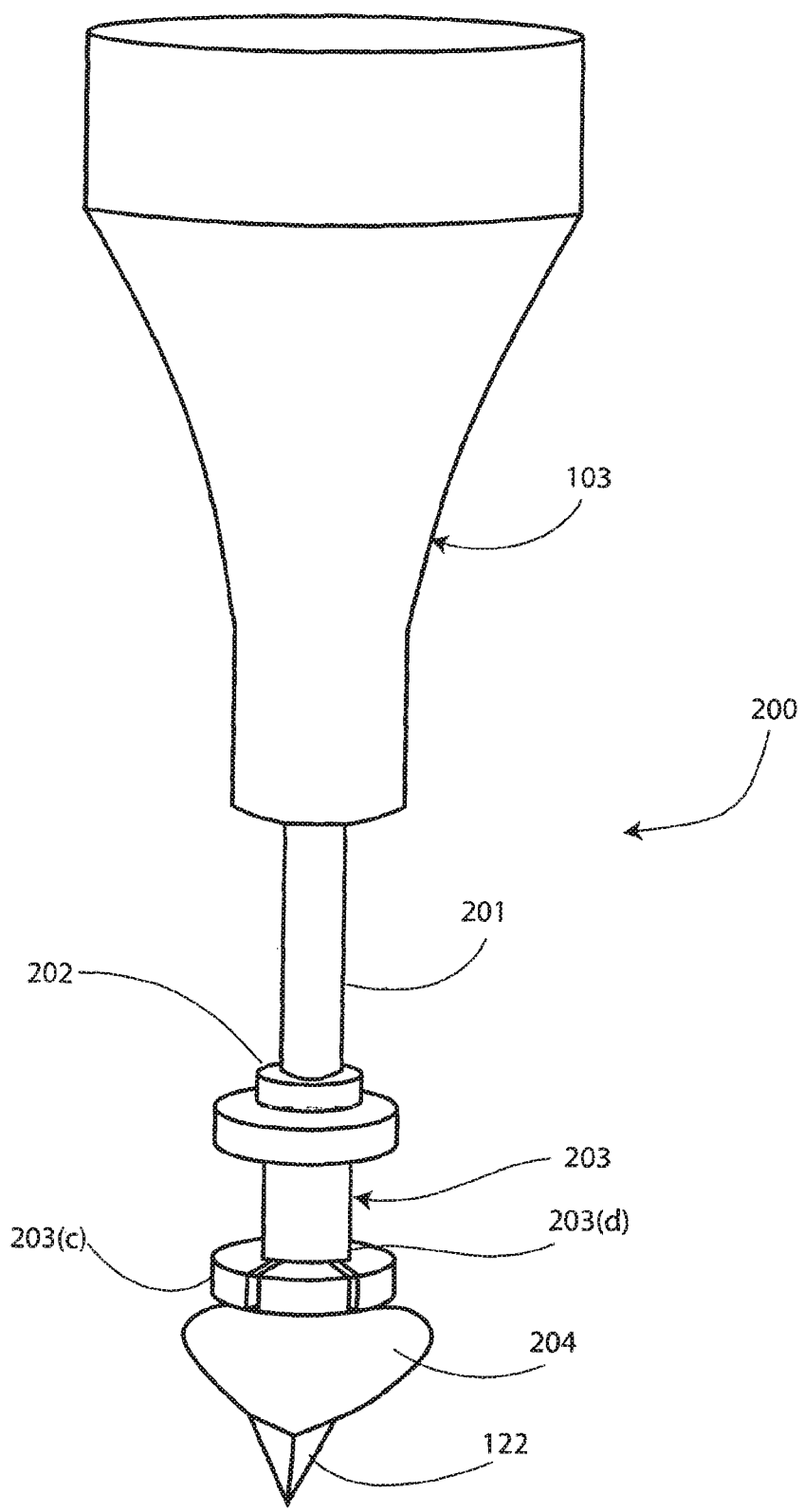

As shown in FIG. 14, the device is placed into a patient's ear. The clinician will adjust the guide collar 104 by pressing the button 112. This will alter the distance between the tip of the head 103 and the tympanic membrane. Once the tympanic membrane is in sharp focus the distance between the tip of the head 103 and the tympanic membrane is at a constant distance 'X'. Once the clinician locates the anterior inferior quadrant of the tympanic membrane they will actuate the trigger 111 to extend the tube insertion assembly 200, shown in FIG. 15, from its sheathed position within the head 103. The tube insertion assembly 200 will penetrate the tympanic membrane through the cutting action of the myringotomy tip 122 until part of the collapsed tube 203 extends through the membrane. The proximal flange 203(a) of the tube 203 will help to prevent penetration too far into the middle ear. Then, actuation of the trigger 110, as shown in FIG. 16, will expand the balloon 204 which is under the tube 203. This balloon inflation, will convert the tube shank 203(b) into a distal flange 203(c). This is because the shank 203(b) is of a material which deforms easily. In other embodiments the centre channel of the tube is also formed to its final state during the procedure. The action of balloon expansion is similar to that of retracting the knife tip 52 in the device 1, force is applied from within to expand the tube to provide the final shape with two flanges, one on each side of the TM. This radial expansion is a reliable and consistent way of deforming the original, collapsed, tube. We believe that it is much more effective than the prior approach of axially clamping the tube between stops.

Figure 17:
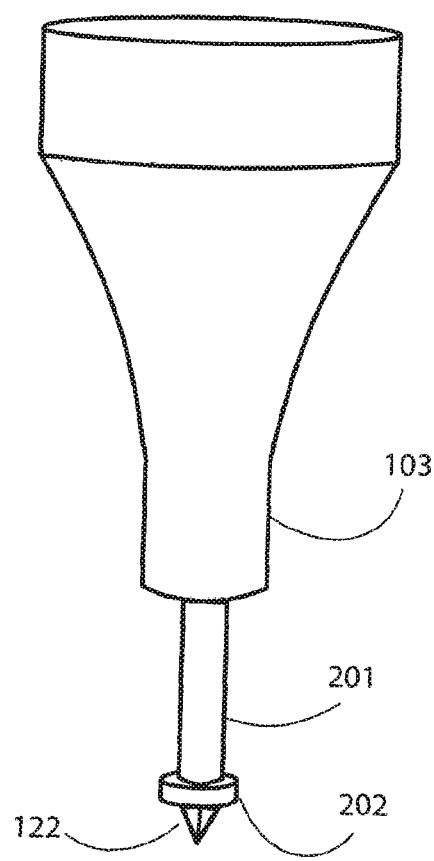
Figure 17:
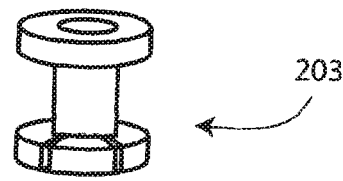

The clinician now releases the trigger 110 to deflate the balloon, and releases the trigger 111 to retract the deflated balloon 204 and the tip 122 through the formed tube 203, as shown in FIG. 17. On retraction the rod, which terminates in an inverted pyramid-shaped tip 122 and holds the balloon 204, will initially retract into the shaft 201. This will aid in ejection of the tube 203 by pushing it against the shoulder 202. Further release of the trigger 111 causes the tube inserter assembly 200 to return into the cylindrical body. The head 103 is then removed from the patient's ear canal.

The action of the balloon is very effective at expanding the tube from within, as it is for other medical technologies such as stent deployment. On the other hand, in the embodiment of FIGS. 1 to 9 the role of the expansion balloon of expanding the tube from within is performed by a non-inflatable feature which is pulled through the collapsed tube using the trigger. This expands the tube to its final, unstressed, state. Once the curved feature has been pulled through the tube, it releases from the tube and the tube remains in the patient's tympanic membrane. The feature may be of a different shape such as spherical, and its shape may not be curved in side view, for example conical.

Figure 18:
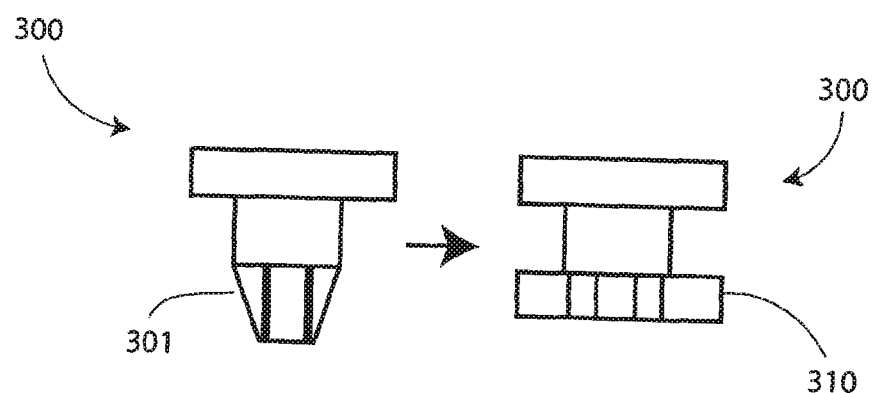

The tympanostomy tube may be made from a metal such as stainless steel or titanium, any of a range of biocompatible plastics such as fluoropolymers (PTFE, PFA, or ETFE), FEP Silicon, HDPE, or a shape memory plastic/metal such as PEEK/Nitinol. The tympanostomy tube in its collapsed state has features present in order to aid in the deployment of the tube. The tympanostomy tube could also have a conical profile (item 300, conical shank 301 as shown in FIG. 18) along its axis so that when the initial myringotomy is made, further actuation of the tube inserter assembly would dilate the myringotomy in the membrane. Also, the device 1 may have a speculum and endoscope arrangement, and the jig 150 may also be used.

The invention is not limited to the embodiments described but may be varied in construction and detail. For example, the tympanostomy tube may be of any other known overall outline shape, as set out above. Also, the spring mechanism in the handle may have a spring with is extended to load it rather than being compressed.

The invention claimed is:

1. A tympanostomy tube applicator comprising:
  a hand-held housing forming a handle;
  a stem extending from the housing and having a shape arranged for engagement in the ear canal;
  a tympanostomy tube inserter for insertion of a tympanostomy tube across a patient's tympanic membrane, the inserter comprising a rod within the stem and having a tip to pierce a patient's tympanic membrane and to support a collapsed tympanostomy tube;
  wherein the housing includes at least one user actuator for operation of the inserter; and
  a cartridge including the stem, the cartridge being releasably connected to the housing to engage the inserter with the actuator;
  wherein the inserter comprises a spring mechanism to pull the rod, and the cartridge is configured to load the spring mechanism as it is connected to the housing, and the actuator is configured to release the spring mechanism to pull the inserter rod, and
  wherein a plug in the handle or the cartridge engages in a socket in the other of the handle or the cartridge, and the inter-engaging plug and socket cause a spring of the spring mechanism to be loaded as the cartridge is connected to the handle.

2. The tympanostomy tube applicator as claimed in claim 1, wherein the cartridge is adapted to be connected to the housing in a rotational and translational action, said action causing the spring mechanism to load and lock the cartridge in place.

3. The tympanostomy tube applicator as claimed in claim 1, wherein the cartridge is adapted to be connected to the housing in a rotational and translational action, said action causing the spring of said spring mechanism to compress.

4. The tympanostomy tube applicator as claimed in claim 1, wherein the cartridge is adapted to be connected to the housing in a rotational and translational action, said action causing the spring of said spring mechanism to compress, and the actuator is reset by rotation of the cartridge in the opposite sense to that for engaging the cartridge to the housing.

5. The tympanostomy tube applicator as claimed in claim 1, wherein the cartridge is pre-loaded with a tympanostomy tube.

6. The tympanostomy tube applicator as claimed in claim 1, wherein the cartridge is pre-loaded with a tympanostomy tube, and said tube is non-removable except by operation of the inserter.

7. The tympanostomy tube applicator as claimed in claim 1, wherein the actuator comprises a button protruding from the housing.

8. The tympanostomy tube applicator as claimed in claim 1, wherein the actuator comprises a button protruding from the housing, and the actuator is configured to transfer pushing motion of the button into a pulling motion of the inserter rod with mechanical advantage.

9. The tympanostomy tube applicator as claimed in claim 1, wherein the actuator comprises a button protruding from the housing, and said button includes ratchets which are attached to a rotating drum which houses a return spring to provide outward bias to the button.

10. The tympanostomy tube applicator as claimed in claim 1, wherein the actuator comprises a button protruding from the housing, and said button includes ratchets which are attached to a rotating drum which houses a return spring to provide outward bias to the button, and wherein the ratchets mate with a slider comprising opposing ratchet teeth, a mating component is mated coaxially to the slider and both are assembled within a compression spring, and a resilient ring is housed within the compression component to provide damping during use.

11. The tympanostomy tube applicator as claimed in claim 1, wherein the actuator comprises a button protruding from the housing, and said button includes ratchets which are attached to a rotating drum which houses a return spring to provide outward bias to the button, and wherein the ratchets mate with a slider comprising opposing ratchet teeth, a mating component is mated coaxially to the slider and both are assembled within a compression spring, and a resilient damper is housed within the compression component to provide damping during use, and wherein the actuator comprises a complementary damper sleeve at an opposite end of the slider, and there is a return spring for the slider.

12. The tympanostomy tube applicator as claimed in claim 1, wherein the stem is in the form of a speculum and includes a channel for an endoscope arranged alongside the inserter.

13. The tympanostomy tube applicator as claimed in claim 1, wherein the stem is in the form of a speculum and includes a channel for an endoscope arranged alongside the inserter; and wherein the housing has an endoscope guide along a side of the housing.

14. The tympanostomy tube applicator as claimed in claim 1, wherein the inserter is adapted to expand from within a distal end of the collapsed tympanostomy tube to provide in situ a distal flange in the tympanostomy tube.

15. The tympanostomy tube applicator as claimed in claim 1, wherein the inserter rod tip comprises a non-inflatable feature adapted to be pulled through a collapsed tube to expand the tube.

16. The tympanostomy tube applicator as claimed in claim 1, wherein the inserter rod tip comprises a non-inflatable feature adapted to be pulled through the collapsed tube to expand the tube; wherein said feature has a curved surface for engagement with the tube to expand it as the tip is pulled through; and wherein said surface is on a proximal side of the tip and is curved and narrows towards the proximal direction.

17. The tympanostomy tube applicator as claimed in claim 1, wherein the inserter rod tip comprises a non-inflatable feature adapted to be pulled through a collapsed tube to expand the tube; and wherein the inserter comprises a shoulder to act as a proximal stop for a tympanostomy tube during expansion of the tympanostomy tube.

18. A tympanostomy tube applicator comprising:
a hand-held housing forming a handle;
a stem extending from the housing and having a shape arranged for engagement in the ear canal;
a tympanostomy tube inserter for insertion of a tympanostomy tube across a patient's tympanic membrane, the inserter comprising a rod within the stem and having a tip to pierce a patient's tympanic membrane and to support a collapsed tympanostomy tube, wherein the housing includes at least one user actuator for operation of the inserter; and
a cartridge including the stem, the cartridge being releasably connected to the housing to engage the inserter with the actuator;
wherein the inserter comprises a spring mechanism to pull the rod, and the cartridge is configured to load the spring mechanism as it is connected to the housing, and the actuator is configured to release the spring mechanism to pull the inserter rod, and
wherein the cartridge is adapted to be connected to the housing in a rotational and translational action, said action causing the spring mechanism to load and lock the cartridge in place.

19. A tympanostomy tube applicator comprising:
a hand-held housing forming a handle;
a stem extending from the housing and having a shape arranged for engagement in the ear canal; and
a tympanostomy tube inserter for insertion of a tympanostomy tube across a patient's tympanic membrane, the inserter comprising a rod within the stem and having a tip to pierce a patient's tympanic membrane and to support a collapsed tympanostomy tube, wherein the housing includes at least one user actuator for operation of the inserter; and
a cartridge including the stem, the cartridge being releasably connected to the housing to engage the inserter with the actuator;
wherein the inserter comprises a spring mechanism to pull the rod, and the cartridge is configured to load the spring mechanism as it is connected to the housing, and the actuator is configured to release the spring mechanism to pull the inserter rod; and
wherein the actuator comprises a button protruding from the housing, and the actuator is configured to transfer pushing motion of the button into a pulling motion of the inserter rod with mechanical advantage.

\* \* \* \* \*